United States Patent [19]
Peloquin et al.

[11] Patent Number: 6,119,503
[45] Date of Patent: Sep. 19, 2000

[54] UNIVERSAL DIE HOLDER ASSEMBLY FOR PRESS BRAKES

[75] Inventors: Wayne F. Peloquin, Forest Lake, Minn.; Timothy J. Mika, Amery; David M. Runk, St. Joseph, both of Wis.; Richard L. Timp, Vadnais Heights; Jason A. Doolittle, Shoreview, both of Minn.

[73] Assignee: Wilson Tool International, Inc., White Bear Lake, Minn.

[21] Appl. No.: 09/285,347

[22] Filed: Apr. 2, 1999

[51] Int. Cl.[7] ........................................ B21J 13/02
[52] U.S. Cl. ........................ 72/481.7; 72/389.4; 72/462
[58] Field of Search ........................ 72/481.1, 481.3, 72/481.5, 481.7, 481.8, 482.6, 482.93, 482.94, 389.4, 389.5, 389.1, 462, 481.9

[56] References Cited

U.S. PATENT DOCUMENTS

| | | |
|---|---|---|
| 784,725 | 3/1905 | Yates . |
| 3,029,858 | 4/1962 | Harper . |
| 3,675,463 | 7/1972 | Hunschauer, Jr. et al. . |
| 3,696,658 | 10/1972 | Hamada . |
| 4,354,374 | 10/1982 | Deguchi . |
| 4,367,644 | 1/1983 | Kramer et al. . |
| 4,535,619 | 8/1985 | Gargrave . |
| 4,586,361 | 5/1986 | Reinhorn et al. ........................ 72/389.4 |
| 4,736,612 | 4/1988 | Russell ...................................... 72/462 |
| 4,787,237 | 11/1988 | Houston et al. . |
| 5,121,626 | 6/1992 | Baldwin . |
| 5,365,767 | 11/1994 | Kitchen et al. ........................ 72/481.1 |
| 5,711,181 | 1/1998 | Mitsuyoshi ............................. 72/481.1 |

FOREIGN PATENT DOCUMENTS 62-72433  4/1987  Japan ..................................... 72/389.4

OTHER PUBLICATIONS

The Cincinnati Shaper Company, "Cincinnati Mechanical Press Brakes", Cover page and pp. 20, 21, 32, 33, 36, 37, Dec. 1959.

*Primary Examiner*—David Jones
*Attorney, Agent, or Firm*—Fredrikson & Byron, P.A.

[57] ABSTRACT

An adjustable die holder for a press brake comprising an elongated base block adapted to be attached to a jaw of a press brake and having a first bore formed therein and a horizontal upper surface; a top plate slidable on the upper surface of the base block. The top plate bears a die holding element and having a second bore formed through it, the second bore being in substantial alignment with the first bore. A die carried by the die holding element has a working surface oriented away from the die holding element. Extending through the first and second bores is an elongated threaded member having external threads. A handle is provided for rotating the threaded member with respect to an internally threaded element which threadingly mates with the elongated threaded member, the handle having an unlocked position wherein the top plate is free to slide upon the upper surface of the base block and a locked position wherein the top plate is locked to the base block.

32 Claims, 7 Drawing Sheets

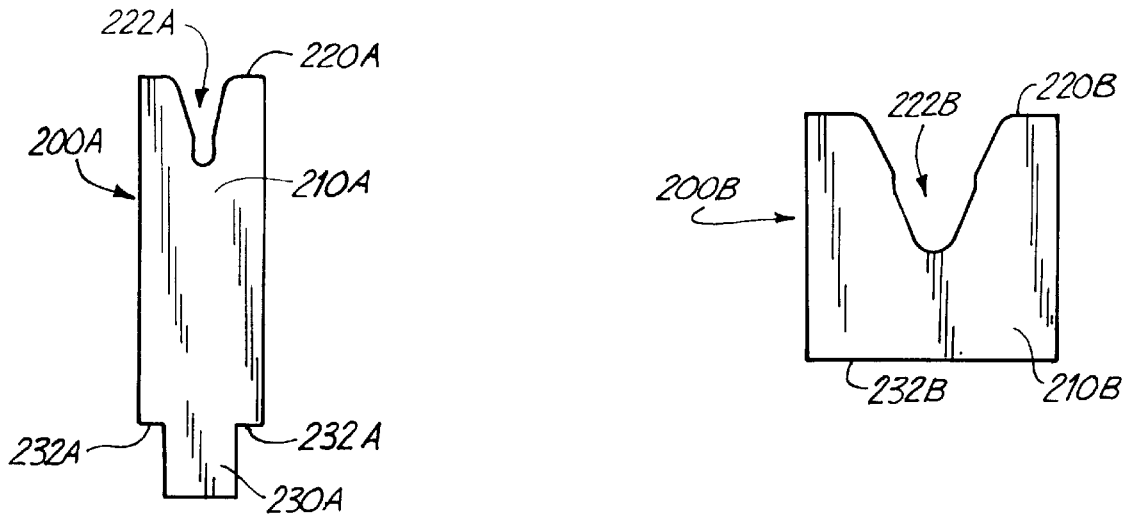
Fig. 5
Fig. 6
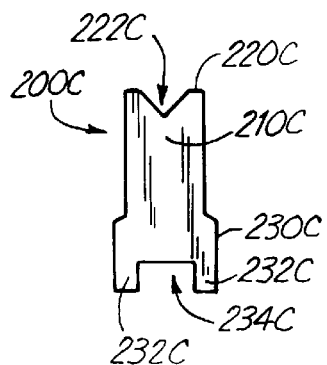
Fig. 7
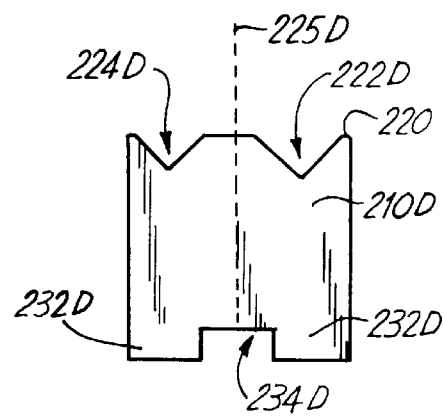
Fig. 8

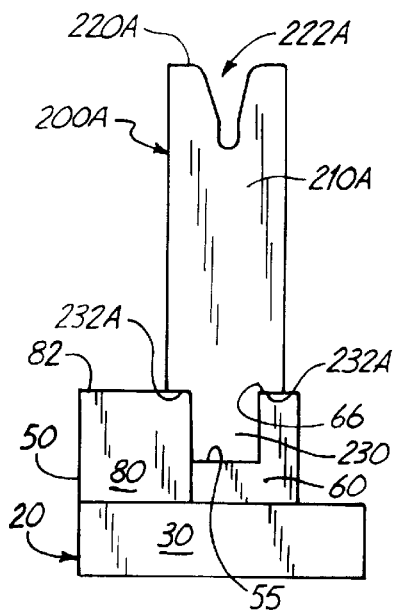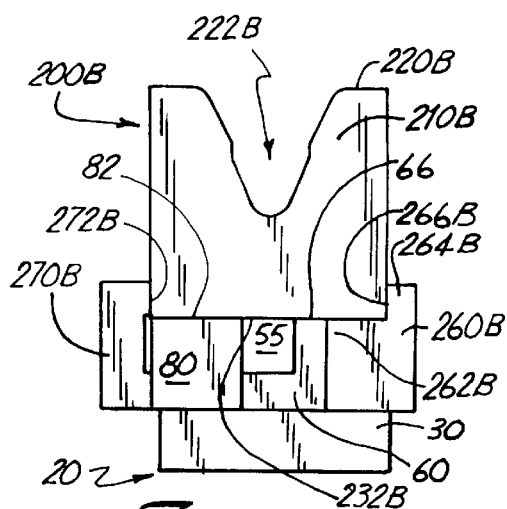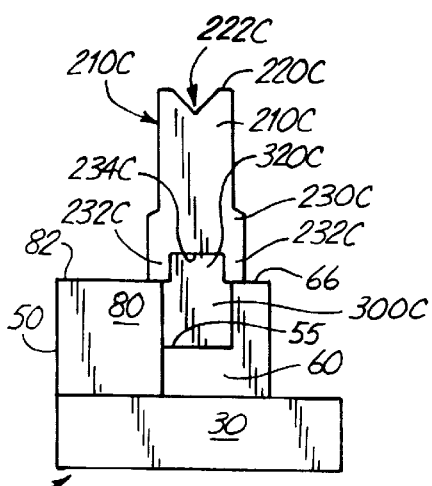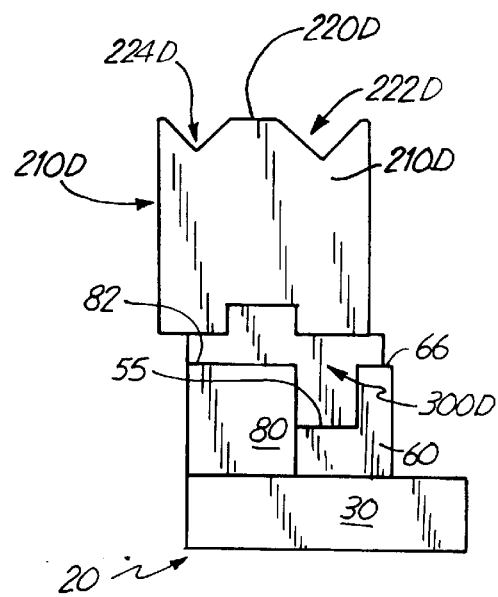

UNIVERSAL DIE HOLDER ASSEMBLY FOR PRESS BRAKES

FIELD OF THE INVENTION

The present invention provides certain improvements for press brakes of the type used to shape sheet metal and the like. More particularly, the invention relates to holders used to releasably hold a forming tool in position in a press brake.

BACKGROUND OF THE INVENTION

Press brakes are used to shape sheet material, typically sheet metal or the like, into a desired shape. Press brakes commonly include a lower table and an upper table, with one of the tables being vertically movable toward the other table. Most commonly, the lower table is movable while the upper table is stationary. Forming tools are mounted to each of these tables so that when the tables are brought toward one another, a workpiece positioned between the forming tables is bent into the desired shape.

It is common for the upper table to include a male forming tool having a bottom, downwardly oriented workpiece-deforming surface of a desired shape, such as a right angled bend. The bottom table will typically carry a die having an upper, upwardly oriented workpiece-deforming surface of an appropriate shape which is aligned with the male forming die. When the die is brought together with the forming tool, a workpiece positioned between the two is pressed by the forming tool into the die and thus is given an appropriate bent shape. The forming tools and dies commonly are horizontally elongated so that workpieces of various widths can be accommodated.

It is often necessary to exchange forming tools and dies when a different bending operation is to be performed. The dies commonly rest in a die holder attached to the bottom table of the press brake. The forming tools usually are carried by tool holders mounted to the upper table of the press brake. It is important to ensure that the dies are precisely aligned with the forming tools to ensure that the respective workpiece-deforming surface of these parts are precisely aligned with one another.

A number of attempts have been made to enable vertical, as opposed to horizontal, adjustment of the die with respect to the lower table. For example, U.S. Pat. No. 4,736,612 (issued to Russell, the teachings of which are incorporated herein by reference) suggests an arrangement utilizing a die holder which rests on a plurality of independently adjustable wedges moveable laterally within a fixed channel. By sliding the wedges from one side to the other beneath the die holder, the die holder can be moved upwardly or downwardly within the channel.

Similarly, U.S. Pat. No 4,586,361 (issued to Reinhorn et al., the teachings of which are also incorporated herein by reference) suggests the use of a specialized wedge to adjust the height of the die mounting tool with respect to the press brake. In particular, Reinhorn et al. propose a wedge which incorporates a specialized rod 57. By adjusting the length of the rod 57, the shape of the wedge is changed, altering the curvature of the wedge along its length.

While the systems of Russell and Reinhorn et al. provide some degree of vertical adjustment, they do not enable an operator to move the die laterally with respect to the table of the press brake. Such a fixed lateral position is acceptable if the precise position of the workpiece-deforming surface of the forming tool does not vary at all from one forming tool to the next. As a practical matter, though, there does tend to be some minor variation in the relative positions of the workpiece-deforming surfaces of the forming tool and the die.

SUMMARY OF THE INVENTION

The present invention provides a horizontally adjustable die holder for a press brake and certain novel die holder arrangements for use in connection with a press brake. In a first embodiment, the invention provides an adjustable die holder for a press brake which includes an elongated base block adapted to be attached to a jaw of a press brake and having a first bore formed therein. A top plate is slidable on an upper surface of the base block, with the top plate bearing a die holding element. A second bore is formed through the top plate and is in substantial alignment with the first bore. A die carried by the die holding element has a working surface oriented away from the die holding element. An elongate threaded member extends generally vertically through the first and second bores, with the threaded member having external threads. A handle, preferably extending generally horizontally outwardly, is adapted to rotate the threaded member with respect to an internally threaded element which threadingly mates with the elongated threaded member. The handle has an unlocked position wherein the top plate is free to slide on the upper surface of the base block and a locked position wherein the top plate is locked to the base block.

In a particularly preferred adaptation of this embodiment, the internally threaded element comprises an inner member and a locking ring. This inner member has internal threads adapted to mate with the external threads of the threaded member and a regular polygonal periphery having n sides. The locking ring has an inner bearing surface defining a regular polygon having n sides or an integral multiple of n sides and an outer bearing surface defining a regular polygon having x sides. Preferably, x is not an integral multiple of n, e.g., n may be six and x may be eight.

In a slightly modified alternative embodiment, the invention provides an adjustable die holder for a press brake which includes an elongated base block adapted to be attached to a jaw of a press brake and having a first bore formed therein. An internally threaded element is positioned adjacent the first bore. A top plate is slidable on an upper surface of the base block, the top plate bearing a die holding element. A second bore is formed in the top plate in substantial alignment with the first bore. A die carried by the die holding element has a working surface oriented away from the die holding element. An elongate threaded member extends downwardly through the first and second bores, with the threaded member having external threads mating with internal threads in the internally threaded element. A handle is attached to the threaded member for rotation therewith. This handle has an unlocked position wherein the top plate is free to slide upon the upper surface of the base block and a locked position wherein the top plate is locked to the base block. If so desired, the internally threaded element of this embodiment may comprise an inner member and a locking ring generally as outlined above.

A different embodiment of the invention provides a die and die holder for a press brake. This arrangement includes an adjustable die holding element comprising a pair of laterally opposed ridges defining therebetween an upwardly open elongated groove. An adapter has an upper rib extending along an upper surface thereof and an elongate shank releasably received in the groove in the die holding element. A die of this embodiment has an upper working surface adapted to work in conjunction with a forming tool to shape sheet material and an elongated channel extending along a bottom surface thereof. The upper rib of the adapter is releasably received in the channel of the die.

Another alternative embodiment of the invention provides a different die and die holder. This die and die holder arrangement includes a die holding element comprising first and second laterally opposed ridges defining therebetween an upwardly open elongated groove. A first lateral extension is releasably carried by the first ridge of the die holding element. The first lateral extension defines an inwardly facing inner surface and defines, with an upper surface of the first ridge, a first die supporting shoulder. A second lateral extension is releasably carried by the second ridge of the die holding element. The second lateral extension defines an inwardly facing inner surface and defines, with an upper surface of the second ridge, a second die supporting shoulder. A first die has a shank received between the inner surfaces of the first and second lateral extensions. A lower surface of the first die rests on the first and second die supporting shoulders. Optimally, the first die is readily exchangeable for a second die, which may have a shank sized to be received in the upwardly open elongated groove of the die holding element.

BRIEF DESCRIPTION OF THE DRAWINGS

FIG. 5 is an end view of one die which may be used with a die holder of the invention;

FIG. 6 is an end view of an alternative die for use with a die holder of the invention;

FIG. 7 is an end view of yet another die which may be used in connection with a die holder of the invention;

FIG. 8 is an end view of a different die which may be used with a die holder of the invention;

FIG. 11 is an end view schematically illustrating how the die of FIG. 5 can be mounted in a die holder of the invention;

FIG. 12 is an end view schematically illustrating how the die of FIG. 6 may be mounted in a die holder of the invention;

FIG. 13 is an end view schematically illustrating how the die of FIG. 7 and the adapter of FIG. 10 may be mounted in one suitable die holder of the invention; and FIG. 14 is an end view schematically illustrating how the die of FIG. 8 and the adapter of FIG. 9 may be used in connection with the illustrated die holder.

DETAILED DESCRIPTION OF THE PREFERRED EMBODIMENTS

Figure 1:
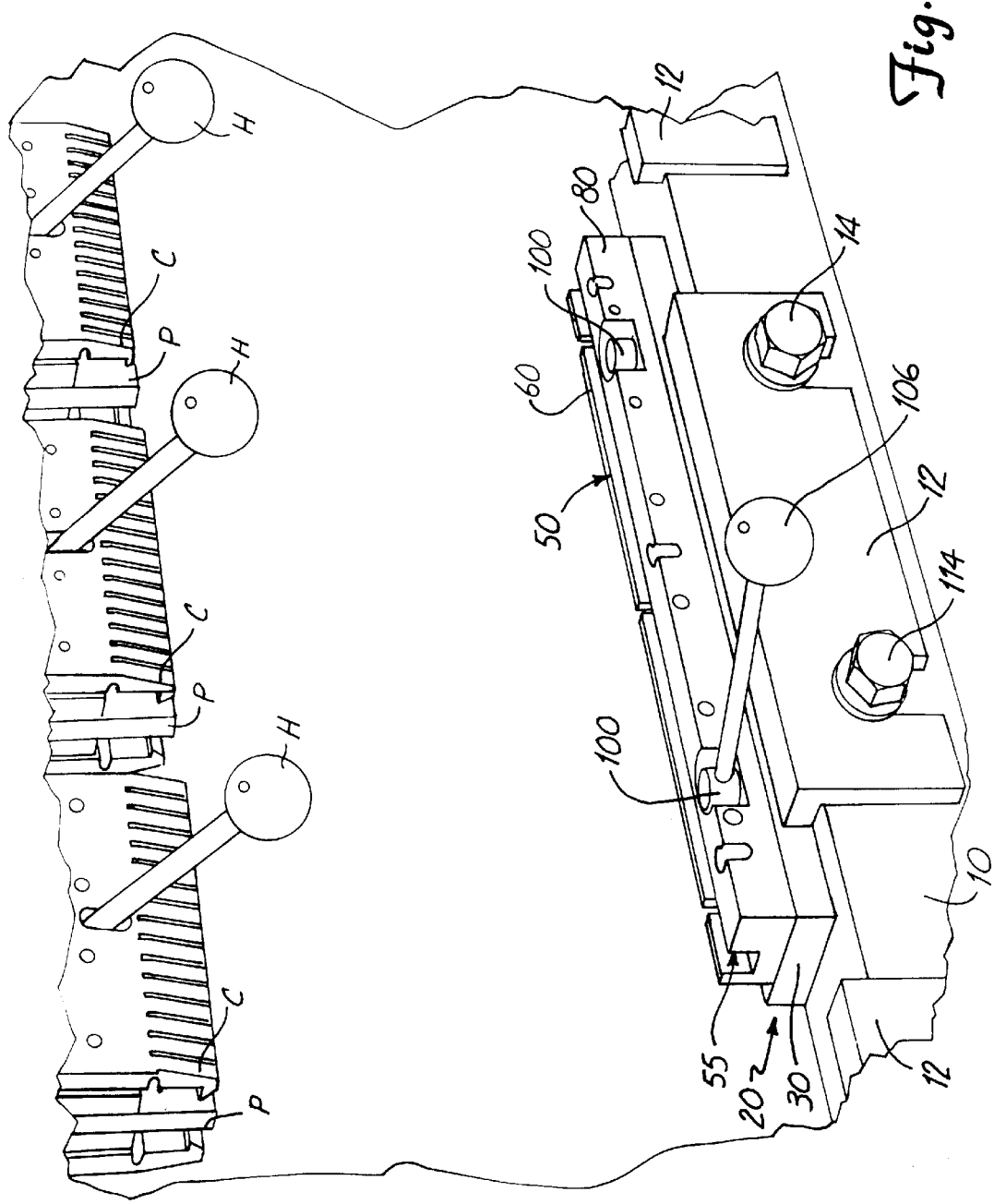
FIG. 1 is a partially broken-away perspective view schematically illustrating how a die holder of the invention may be used in a press brake.

FIG. 1 schematically illustrates a press brake utilizing a die holder 20 in accordance with the present invention. The press brake includes a series of horizontally aligned clamps C which are used to clamp forming tools (not shown) against a support plate.

The clamp C is brought into clamping engagement with the forming tool by means of a handle H. A press brake forming tool holder such as that illustrated in FIG. 1 is disclosed in detail in PCT International Publication No. WO 99/01240 (the teachings of which are incorporated herein by reference). This forming tool holder is shown in FIG. 1 solely for purpose of illustration. The die holder 20 of the invention can be used in any press brake without requiring that any specific forming tool holder be used therewith.

The die holder 20 is mounted on a lower table 10 of the press brake. The die holder includes a base block 30 and a top plate 50. The base block may be attached to the lower table 10 in any suitable fashion. For example, the base block may be held in place on the lower table by means of a pair of opposed brackets 12. (Only one of the opposed brackets is shown in FIG. 1, the other of the pair being positioned behind the die holder 20 and thus being obscured from view.) The bracket desirably may be adjusted to release the base block 30. This releasable attachment of the die holder 20 to the lower table 10 permits the die holder 20 to be selectively retrofitted to any standard press brake.

Figure 2:
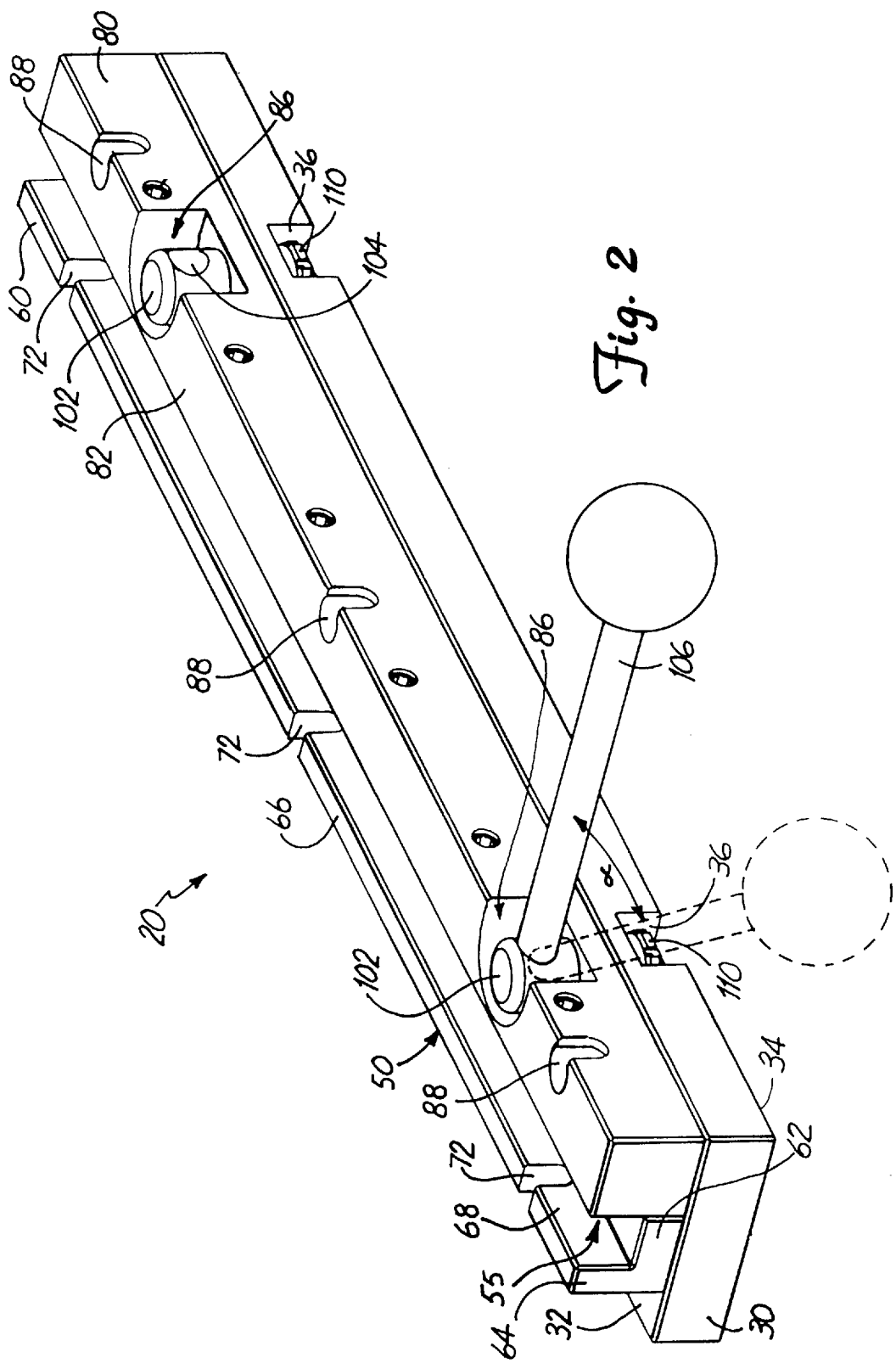
FIG. 2 is a perspective isolational view of a die holder in accordance with one embodiment of the invention.
Figure 3:
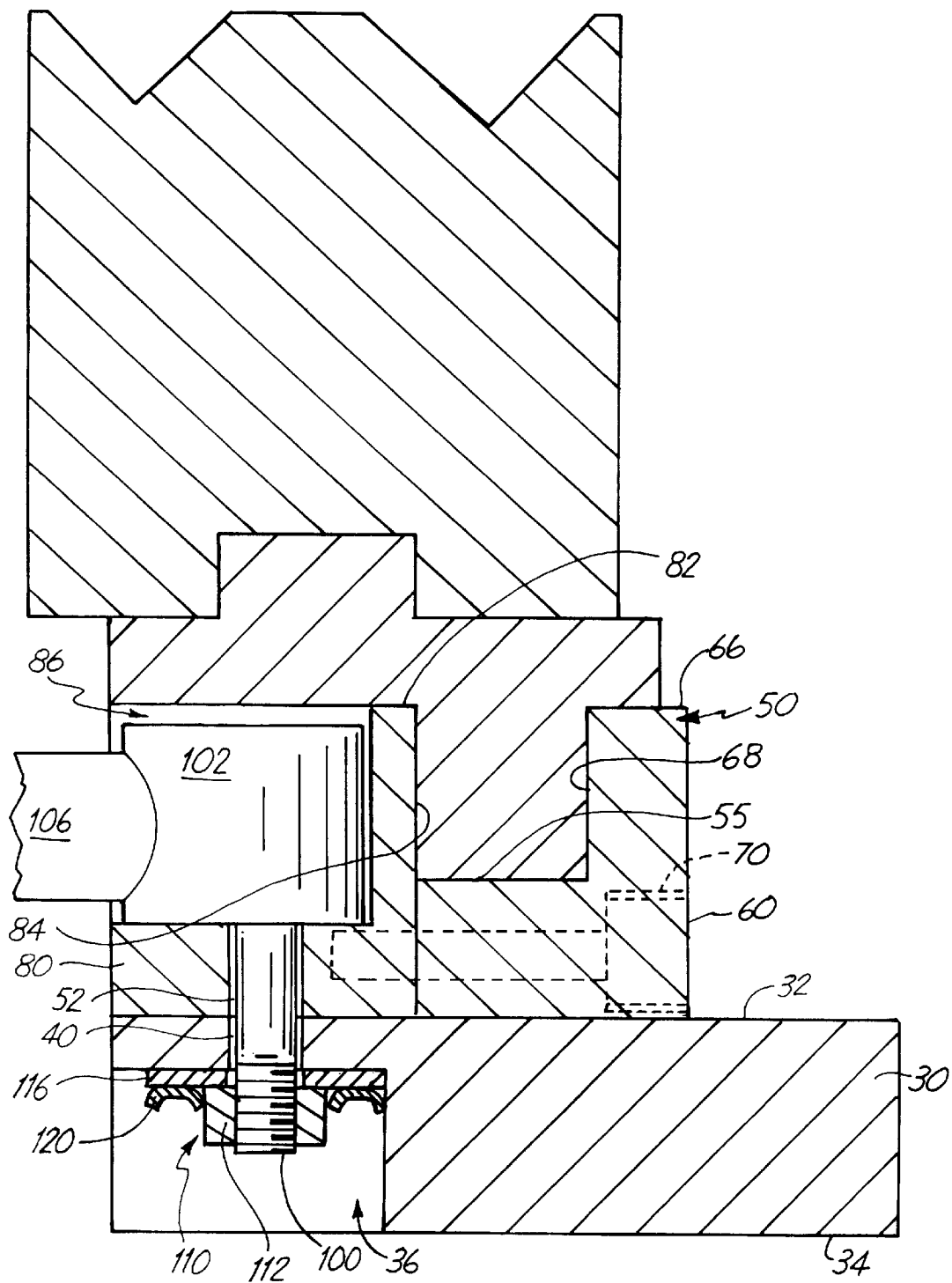
FIG. 3 is an isolational cross-sectional view of the die holder of FIG. 2 with a die carried thereby.

FIG. 2 and 3 illustrate the die holder 20 of FIG. 1 in more detail. As shown in these figures, the base block 30 includes a generally flat, horizontally oriented upper surface 32 and a substantially parallel flat lower surface 34. For reasons explained in more detail below, the lower surface of the base block 30 desirably includes a recess 36 within which an internally threaded element 110 is retained.

The top plate 50 is slidably carried by the upper surface 32 of the base block 30. This top plate 50 desirably carries a die holding element, the nature of which can vary depending upon the nature of the dies to be used with the die holder 20. If so desired, the die holding element can comprise a C-clamp (not shown) similar to the clamp C use in the tool holder of FIG. 1. Since the die which is to be carried by the die holder will tend to remain in place under the force of gravity, though, such a positive restraining force generally is not needed and a more passive positioning arrangement may be used instead.

In the illustrated embodiment, the top plate 50 has an elongated groove 55 extending along the entire length thereof. As explained below, a portion of an adapter plate can be received within this elonganted groove to hold the die in place with respect to the forming tool carried by the clamp C of the upper table.

If so desired, the top plate may be integral in construction, being molded or machined from a single piece of metal. In the the illustrated embodiment, though, the top plate 50 is formed of an L-shaped member 60 and a rectangular member 80 attached to one another by means of an attachment screw 70 (shown in phantom lines in FIG. 3).

The L-shaped member 60 generally includes a bottom leg 62 with a first ridge 64 extending generally perpendicularly upwardly therefrom. The first ridge 64 has an upper surface 66 which is desirably generally horizontal and parallel to the upper surface 32 of the base block 30. The first ridge 64 also has an innerface 68 which is oriented toward and is generally parallel to the rectangular member 80. The rectangular member 80 includes an upper surface 82 and an innerface 84 (best seen in FIG. 3). As with the L-shaped member 60, the upper surface 82 of the rectangular member is desirably generally horizontal and parallel to the upper surface 32 of the base block. The innerface 84 of the rectangular member is parallel to the innerface 68 of the L-shaped member. The innerface 68 and bottom leg 62 of the L-shaped member and the innerface 84 of the rectangular member together define the elongated groove 55 in the top plate 50.

As best seen, in FIG. 3, the top plate 50 is attached to the base block 30 by means of an elongated threaded member 100. This elongated threaded member passes through a first bore 40 which passes through the base block 30 and a second bore 52 which passes through the top plate 50. In use, the second bore 52 is in substantial alignment with the first bore 40 to permit the threaded member 100 to pass through both bores without binding.

At least one of the first and second bores 40, 52 should have an internal dimension which is larger than the external diameter of the threaded member 100. The purpose of having at least one of the bores larger than the shaft of the threaded member is to permit the threaded member 100 to move within at least one of the bores, thereby permitting lateral movement of the top plate 50 with respect to the base block 30. In the illustrated embodiment, the first and second bores are both substantially the same size and, therefore, are both larger than the outer diameter of the threaded member 100. If so desired, one of these two bores may more closely engage the shaft of the threaded member 100. For example, the first bore 40 may fairly closely encircle the shaft of the threaded member 100 while the second bore is larger, permitting a certain range of movement of the top plate 50 with respect to the base block 30. In such an embodiment, there should be sufficient clearance between the first bore 40 and the shaft of the threaded member to permit the threaded member to rotate about its axis within the first bore.

If so desired, one or both of the first and second bores can be generally circular in cross section and have an inner diameter larger than the exterior diameter of the cylindrical threaded member 100. This would permit the top plate 50 to move both laterally (i.e., to the left or right in FIG. 3) and longitudinally with respect to the base block 30. This may be particularly advantageous in an arrangement such as that shown in FIGS. 1 and 2 wherein there is a pair of longitudinally spaced threaded members connecting the top plate 50 and base block 30 at two longitudinally spaced locations. This permits adjustment of the orientation of the elongated groove 55 with respect to the clamps C of the upper table of the press brake and the forming tools carried thereby (not shown).

It may be preferred to fix the orientation of the groove 55 to ensure that it will at all times remain parallel to the support plates P of the upper table of the press brake. In such a circumstance, one or both of the first and second bores 40, 52 may take the form of a laterally elongated oval, ellipse or slot. Such a slot-like bore may be elongated in a lateral direction generally perpendicular to the longitudinal axis of the groove 55. The narrow dimension of this elongated bore may be just slightly greater than the outer diameter of the threaded member 100 to limit longitudinal movement of the threaded member within the slot, yet permit it to slide laterally from one end of the slot to the other. The slot need not be very long, it is anticipated that the slot may have an aspect ratio (i.e., a lateral length divided by its longitudinal width) of no more than 2, with an aspect ratio on the order 1.2–1.4 being acceptable.

The threaded member 100 may be used to clamp the top plate 50 against the base block 30 to restrict relative motion there between when the top plate 50 has been'positioned in the desired orientation with respect to the upper table of the press brake. In the illustrated embodiment, the threaded member 100 has an enlarged head 102 at its upper end and an internally threaded element 110 is received within the recess 36 in the lower surface of the base block 30. In order to facilitate turning of the threaded member with respect to the internally threaded element, a handle 106 may be attached to the head of the threaded member. While the handle may be permanently attached thereto, a handle projecting from the die holder 20 can interfere with the feeding sheet material into the press brake for bending. Accordingly, in a preferred embodiment, the handle is releasably received within an opening (104 in FIG. 2) in the head 102, permitting the handle to be inserted therein to rotate the threaded member. When the top plate 50 is locked in place, the handle may be removed therefrom and stored in a location where it will not interfere with operation of the press brake.

In the illustrated embodiment, the handle 106 has a relatively limited range of motion. In particular, the handle abuts against the opposite edges of the bay 86 and the rectangular member 80, leaving the handle a maximum angle of motion identified as α in FIG. 2. One edge of this range of motion (shown in solid lines in FIG. 2) may be considered an unlocked position of the handle wherein the top plate is free to slide upon the upper surface 32 of the base block. The other end of this range of motion (e.g., the position indicated in phantom lines FIG. 2) may be considered a locked position of the handle, wherein the top plate is locked to the base block by the clamping action of the threaded member 100.

The illustrated embodiment has a threaded member extending downwardly through the first and second bores 40, 52 and internally threaded element 110 positioned beneath the first bore 40. It should be understood, though, that this orientation can be varied if so desired. For example, the internally threaded member can be turned around such that it has a head which is positioned beneath the first bore 40 and a shaft which extends upwardly through the first and second bores. An internally threaded member may be releasably attachable to the handle 106 at a location above the second bore 52. Either way, movement of the handle from one position to the other will rotate the threaded member with respect to the internally threaded element selectively locking and unlocking the relative positions of the top plate and the bate block.

Any suitable internally threaded element may be used. For example, the interior of the first bore 40 in the base block 30 can be internally threaded. This will permit an operator to clamp the top plate 50 between the upper surface 32 of the base block and the head 102 of the threaded member by moving the handle from its unlocked position to its locked position.

In the illustrated embodiment, though, the internally threaded element 110 comprises a separate component which is positioned in a recess 36 in the base block 30. As best seen in conjunction with FIGS. 3 and 4, the preferred internally threaded element 110 of the drawings includes a conventional nut 112 and a locking ring 120. The nut has internal threads which are adapted to mate with the external threads which extend along at least a lower portion of the threaded member 100. The nut also has a periphery 114 defining a regular polygon having n sides. In the illustrative embodiment of FIG. 4, the nut is a standard hexagonal nut and the periphery 114 has 6 sides of equal length, i.e., n=6. If so desired, a standard washer 116 may be positioned between the nut 112 and the base block 30.

The primary purpose of the locking ring 120 is to limit rotation of the nut 112 within the recess 36. One could achieve this function simply by making the recess 36 in the base block slightly smaller than the maximum transverse dimension of the nut 112 so that the nut could not spin within that recess. However, this limits adjustment of the rotational position of the nut with respect to the base block. In particular, for each complete rotation of the nut with respect to the recess, the nut would only have 6 discrete positions, limiting the change between one angular position of the nut to the next angular position to 60.

Figure 4:
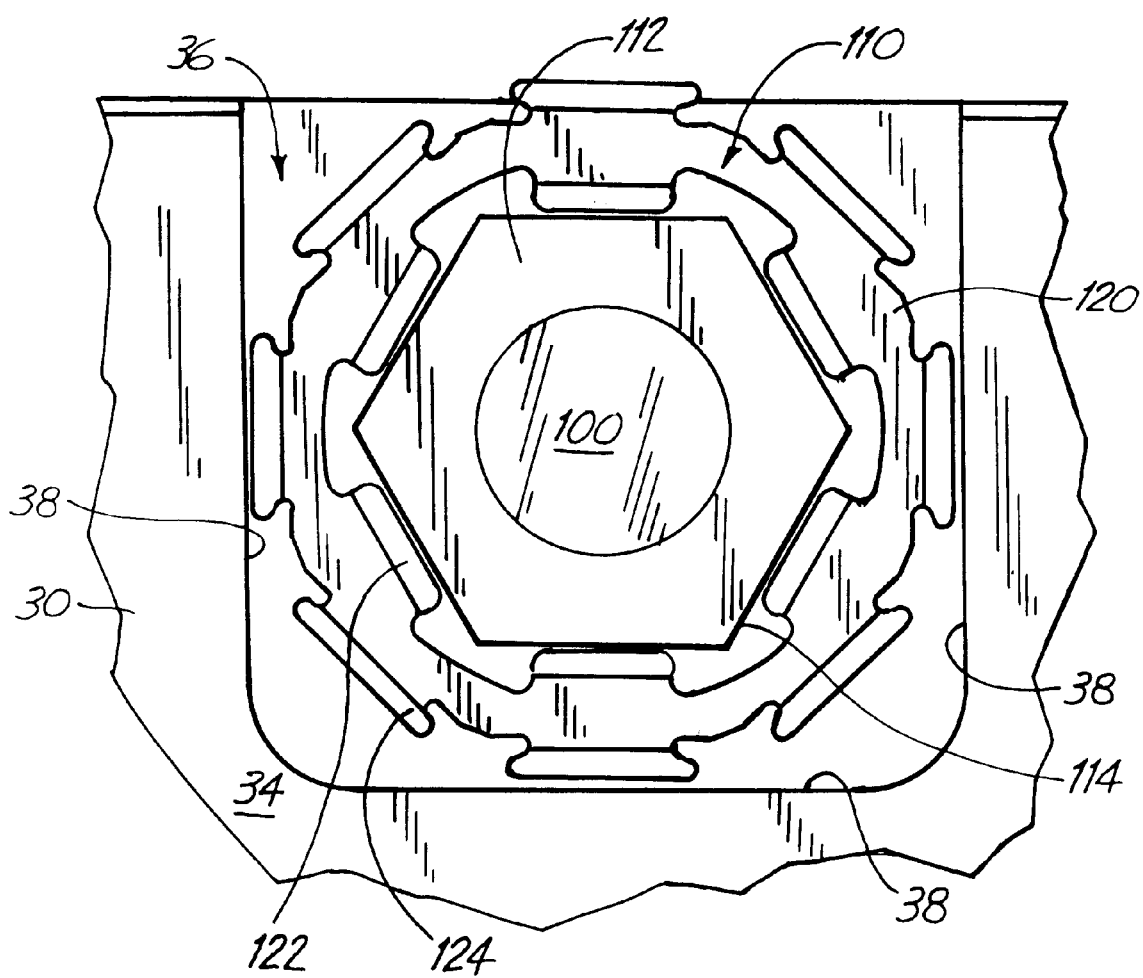
FIG. 4 is a bottom view of an internally threaded element which may be used in the die holder of FIGS. 2 and 3.

The locking ring 120 shown in FIG. 4 permits a significantly higher degree of resolution of the angular position of the nut with respect to the base block. The locking ring 120 has an inner bearing surface having n sides, or in integral multiple of n sides. For example, if the nut had 4 sides, the inner bearing surface may have 4, 12 or even 18 sides. The embodiment shown in FIGS. 3 and 4 is suitable for relatively inexpensive stamping from sheet metal, with the inner bearing surface 122 being defined as n separate flanges which are directed inwardly to bear against the periphery 114 of the nut 112.

The outer bearing surface 124 of the locking ring 120 has a different number of sides than the number of sides provided on the nut. Stated in another manner, the outer bearing surface of the locking ring has x sides, where x is not equal to n. In the illustrated embodiment, x=8, which is not an integral multiple of n when n=6.

As a consequence of this arrangement, one can achieve relatively fine adjustment of the position of the nut with respect to the recess 36 by varying the position of the nut within the locking ring and the position of the locking ring within the recess 36. One full rotation of the nut 112 within the locking ring 120 will define six discreet positions, separated by 60° from one another. The outer bearing surface 124, of the locking ring has eight sides, yielding eight different positions within a single rotation, each differing by 45° from the adjacent positions. The position of the nut with respect to the base block 30 can be adjusted even more finely, though, by independently adjusting the relative positions of the nut and the locking ring with respect to the base block. For example, by advancing the nut by one position (60°) within the locking ring and turning the locking ring one position (45°) the opposite. direction, one can achieve a net advancement of the nut by a mere 15°.

This relatively fine adjustability of the position of the nut with respect to the base block 30 yields a significant practical advantage to operation of the illustrated die holder 20. As noted above, when the handle is in its unlocked position (shown in phantom lines in FIG. 2), the top plate 50 is free to slide along the upper surface 32 of the base block; moving the handle through the angle to its locked position (shown in solid lines in FIG. 2) should firmly fix the positions of the top plate 50 and base block 30. The pitch of the threads on the threaded member should be steep enough to ensure that movement of the handle through the angle α will raise and lower the head 102 of the threaded member sufficiently to release or clamp the top plate 50 and base block 30 with respect to one another. By allowing a relatively fine adjustment of the position of the nut 112 with respect to the threaded member 100, the nut can be positioned on the threaded member in a precise location to ensure that the unlocked position of the handle will permit movement of the top plate and base block 30 with respect to one another while rotating the handle through the angle α will lock these elements in place.

The die holder 20 of this embodiment of the invention enables to working surface of a die to be precisely aligned with the working surface of a forming tool of the press brake with great ease. With reference to FIG. 1, a die would be positioned in the channel 55 in the top plate 50 of the die holder and a forming tool would be held in place against the support plate P by the clamp C of the upper table of the press brake. With the threaded members 100 positioned so that the top plate 50 is free to slide on the upper surface 32 of the base block, the top plate may be positioned so that the die is approximately aligned with the forming tool.

The upper and lower tables of the press brake may then be brought closer to one another, preferably manually and relatively slowly rather than with the full force and speed of a forming stroke of the press brake. The working surface of the forming tool is brought into engagement with the working surface of the die, with any visibly necessary adjustments to the alignment of these parts being corrected by manually moving the top plate with respect to the base block. Once this coarse adjustment is made, the forming tool and die may be brought closer together. The working surfaces of these elements will tend to slide against one another until they are precisely aligned, with the force of the forming tool urging the die into the desired position. Once the die is in its desired position, the handle 106 may be inserted into the head of one threaded member 100 and moved into its locked position, effectively locking the top plate 50 to the base block 30. The handle can then be withdrawn and attached to the head of the other threaded member and moved into its locked position, further locking the top plate and the base block from relative movement.

As a consequence, the die holder 20 shown in the drawings represents a significant advance over the current state of the art. Most prior art die holders for use in press brakes do not allow any significant horizontal realignment of the die held therein with respect to a forming tool. As a consequence, the tool and the die will not always be precisely aligned, leading to increased wear on the tool and die. The die holder 20 not only permits such adjustment, but provides a simple method for very precisely aligning the tool and the die, using the working surfaces of the tool and the die themselves to ensure proper positioning.

FIGS. 5–8 illustrate four possible embodiments of different dies which can be used in connection with the die holder 20 shown in FIGS. 1–4. Each of FIGS. 5–14 is a schematic end view, intended primarily to show the cross sectional shape of the elements shown therein. It should be understood that each of the illustrated dies are elongated in a longitudinal direction, i.e., in a direction perpendicular to the plane of the paper bearing these drawings. For example, each of the dies 200A–200D in FIGS. 5–8 may have the same length as the elongate groove 55 in the top plate 50 of the die holder 20 shown in perspective view in FIGS. 1 and 2.

Turning first to FIG. 5, this die 200A has an elongate body 210A with an upper working surface 220A and a shank 230A having an elongate ridge extending along a bottom surface thereof. The precise shape of the working surface 220A will vary depending on the shape of the working surface of the forming tool with which the die is to be used and the desired bend in the sheet material to be achieved using this tool and die combination. In FIG. 5, this working surface includes an elongate V-shaped notch 222A which extends along the entire length of the die 200A.

The shank 230A of this dies 200A is optimized to fit directly in the groove 55 of the top plate 50 of the die holder 20. The elongate ridge of the shank defines a pair of generally horizontal shoulders, with one shoulder extending along either side of the ridge. As best seen in FIG. 11, the shank 230A of the die 200A is adapted to be received in the elongate groove 55 of the top plate of the die, with one of the shoulders 232A resting on the upper surface 66 of the L-shaped member 60 and the other shoulder 232A resting on the upper surface 82 of the rectangular member 80. Preferably, the ridge of the shank 230A is adapted to substantially fill the groove 55 to limit lateral movement twisting of the die 200A in use.

FIGS. 6 and 12 illustrate an alternative die 200B which is attached to the die holder 20 using a special attachment. The die 200B generally includes a body 210B, an upper working surface 220B with a V-shaped notch 222B therein and a lower surface 232B. The notch 222B is substantially wider and deeper than the notch 222A of FIG. 5, but this is largely for purposes of illustrating the possible variation in the shapes of the working surfaces typical of press brake dies. Unlike the embodiment of FIGS. 5 and 11, there is no elongate ridge defining a readily identifiable shank 230A. Instead, the body 210B may be said to define the shank.

As shown in FIG. 12, the die 200B is held in place atop the die holder 20 using a pair of lateral extensions 260B and 270B. The first lateral extension 260B is carried by the L-shaped member 60 of the top plate 50 and may itself be generally L-shaped, with a bottom leg 262B and a ridge 264B having an inner face 266B. The bottom leg 262B is desirably sized to abut the L-shaped member 60 of the top plate such that the top of the leg 262B is flush with the upper surface 66 of the L-shaped member 60. As a consequence, the first lateral extension 260B and the L-shaped member 60 together define a first die supporting shoulder. The second lateral extension 270B is carried by the rectangular member 80 of the top plate and may be generally C-shaped, as shown. The inner face 272B of the second lateral extension abuts the upper surface 82 of the rectangular member 80, defining therewith a second die supporting shoulder. The lower surface 232B of the die 200B rests on these die supporting shoulders, with the inner face 266B of the first extension and the inner face 272B of the second extension being spaced from one another approximately the width of the body 210B of the shank to precisely position the die with respect to the die holder 20.

The first and second lateral extensions 260B, 270B can be attached to the L-shaped member 60 and rectangular member 80, respectively, of the top plate in any suitable fashion, e.g., by means of set screws or the like. If so desired, though, the top plate 50 of the die holder may be specially adapted to permit such lateral extensions to be quickly and easily attached to or detached therefrom. Looking to FIG. 2, the L-shaped member 60 has three attachment notches 72 spaced along the length of the ridge 64. Returning to FIG. 12, the first lateral extension 260B may be provided with three separate knobs (not shown) spaced along the inner edge thereof at locations designed to fit in these notches 72. Each of the knobs may have a shaft sized to be received in a notch 72 and an enlarged head that would rest in the groove 55, holding the first extension 260B in place, but permitting an operator to readily detach the extension by lifting the knobs up out of the notches 72. Similarly, the second extension 270B can be provided with a plurality of knobs adapted to be received in attachment notches 88 in the rectangular member 80.

Figure 10:
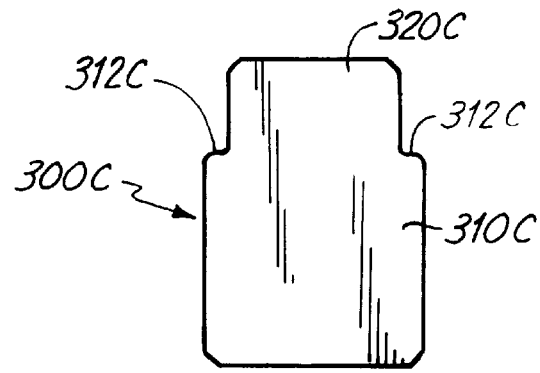
FIG. 10 is an end view of an alternative adapter which may be used to mount a die in a die holder of the invention.

FIGS. 7 and 13 illustrate another die 200C for use with the die holder 20 and FIG. 10 illustrates an adapter 300C used to facilitate holding the die 200C by the die holder. This die includes a body 210C, an upper working surface 220C with a V-shaped notch 222C therein and a shank 230C. The shank 230C of this embodiment includes an elongated channel 234C extending along the bottom surface thereof, with one downwardly extending tab 232C on either side thereof. The adapter 300C of FIG. 10 generally includes an elongate shank 310C adapted to be received in the groove 55 in the top plate and an upper rib 320C extending along an upper surface of the adapter. As best seen in FIG. 13, the upper rib 320C is sized to be releasably received in the elongated channel 234C of the die. Optimally, the shank 310C of the adapter is sized so that the shoulders 312C thereof will be aligned with the upper surfaces 66,82 of the top plate 50.

Figure 9:
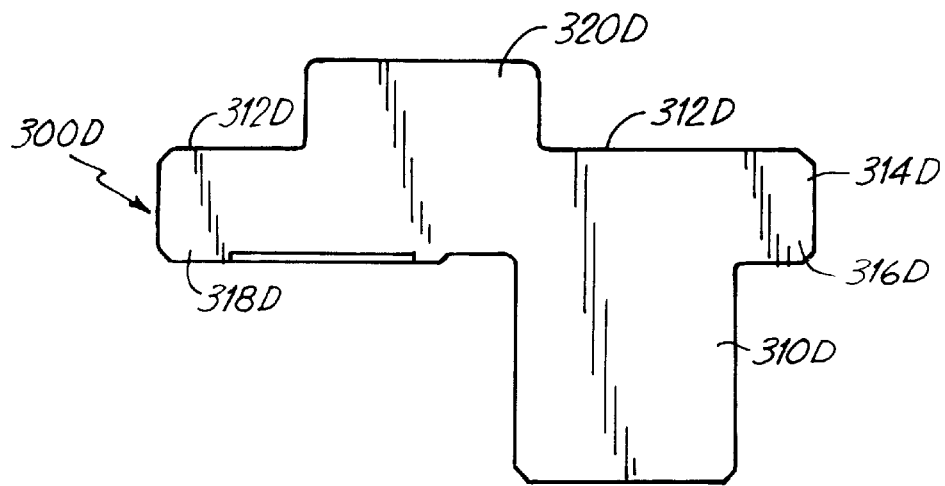
FIG. 9 is an end view of one adapter which may be used to mount a die in a die holder of the invention.

FIGS. 8 and 14 illustrate another die 200D for use with the die holder 20 and FIG. 9 illustrates an adapter 300D used to facilitate holding the die 200D by the die holder. This die includes a body 210D, an upper working surface 220D with a V-shaped notch 222D therein. Unlike the other dies 200A–200C, the working surface 220D of the die 200D in FIGS. 8 and 14 also has a second V-shaped notch 224D, with the center line of each of the notches being spaced the same distance from a midline plane 225D vertically bisecting the die. The die also includes an elongated channel 234D extending along the bottom surface of the body between two spaced-apart tabs 232D.

The adapter 300D includes a shank 310D and an upper rib 320D extending long the adapter's upper surface. The shank 310D is sized to be releasably received in the groove 55 n the top plate of the die holder while the upper rib 320D is sized to be releasably received in the channel 234D in the die. Unlike the adapter 300C, the upper rib 320D of this adapter 300D is not vertically aligned with the shank 310D. Instead, the upper rib is laterally offset from the shank, with a central plate 314D connecting the shank and the rib. The plate 314D has a lower shoulder 316D adapted to rest on the upper surface 66 of the L-shaped member 60 and another lower shoulder 318D adapted to rest on the upper surface 82 of the rectangular member 80. An upper shoulder 312D is positioned on either side of the upper rib 320D, with each such shoulder being positioned to supportingly abut a downwardly extending tab 232 of the die.

One advantage of the dual notch die 200D and offset adapter 300D of this embodiment is that it permits one to alter the shape of the working surface positioned beneath the forming tool (not shown). In the arrangement shown in FIG. 14, the first notch 222D of the die is positioned vertically above the groove 55 in the top plate. Ideally, this groove is positioned beneath the working surface of the forming tool, ensuring that the first notch will precisely mate with the forming tool. If it is desired to change the shape of the effective working surface of the die (either alone or in conjunction with a change in the forming tool), one can turn the die 200D 180° in a horizontal plane. Since the center lines of the first and second notches 222D and 224D are positioned the same distance from the midline plane 225D of the die, this will position the second notch 224D at the same location with respect to the groove 55 in the top plate of the die holder.

While a preferred embodiment of the present invention has been described, it should be understood that various changes, adaptations and modifications may be made therein without departing from the spirit of the invention and the scope of the appended claims.

What is claimed is:

1. An adjustable die holder for a press brake comprising:
   a) an elongated base block adapted to be attached to a jaw of a press brake and having a vertical first bore formed therein and a horizontal upper surface;
   b) a top plate slidable on the upper surface of the base block, the top plate bearing a die holding element and having a second bore formed therethrough, the second bore being in substantial alignment with the first bore;

c) a die carried by the die holding element, the die having a working surface oriented away from the die holding element;

d) an elongated threaded member extending through the first and second bores, the threaded member having external threads;

e) an internally threaded element which threadingly mates with the elongated threaded member and that is positioned beneath the first bore in the base block, and a handle for rotating the threaded member with respect to said internally threaded element, the handle having an unlocked position wherein the top plate is free to slide upon the upper surface of the base block and a locked position wherein the top plate is locked to the base block.

2. The adjustable die holder of claim 1 wherein the internally threaded element comprises an inner member and a locking ring seated in a recess in the base block having an internal abutting surface; the inner member having internal threads adapted to mate with the external threads of the threaded member and a regular polygonal periphery having n sides; the locking ring having an inner bearing surface defining a regular polygon having an integral multiple of n sides and an outer bearing surface which engages the internal abutting surface of the recess to limit rotation of the locking ring with respect to the base block.

3. The adjustable die holder of claim 1 wherein the internally threaded element comprises an inner member and a locking ring; the inner member having internal threads adapted to mate with the external threads of the threaded member and a regular polygonal periphery having n sides; the locking ring having an inner bearing surface defining a regular polygon having an integral multiple of n sides and an outer bearing surface defining a regular polygon having x sides, wherein x is not an integral multiple of n.

4. The adjustable die holder of claim 3 wherein n is six and x is eight.

5. The adjustable die holder of claim 1 wherein the second bore is larger than the first bore.

6. The adjustable die holder of claim 1 wherein the second bore is elongated.

7. The adjustable die holder of claim 6 wherein the second bore has an aspect ratio of no more than two.

8. The adjustable die holder of claim 1 wherein the die holding element comprises an upwardly open elongated groove in the top surface of the top plate.

9. The adjustable die holder of claim 8 wherein the die has a rib extending along a bottom surface thereof, the rib being received in the groove in the top plate.

10. The adjustable die holder of claim 8 wherein the second bore is elongated in a direction perpendicular to a major axis of the groove in the top plate.

11. An adjustable die holder for a press brake comprising:

a) an elongated base block adapted to be attached to a jaw of a press brake and having a first bore formed therein;

b) a top plate slidable on an upper surface of the base block, the top plate bearing a die holding element and having a second bore formed therethrough, the second bore being in substantial alignment with the first bore;

c) a die carried by the die holding element, the die having a working surface oriented away from the die holding element;

d) an internally threaded element being positioned adjacent the first bore the internally threaded element comprising an inner member and a locking ring; the inner member having internal threads adapted to mate with the external threads of the threaded member and a regular polygonal periphery having n sides; the locking ring having an inner bearing surface defining a regular polygon having an integral multiple of n sides and an outer bearing surface defining a regular polygon having x sides wherein x is not an integral multiple of n, and an elongated threaded member extending through the first and second bores, the threaded member having external threads mating with internal threads of the internally threaded element; and e) a handle attached to the threaded member for rotation therewith, the handle having an unlocked position wherein the top plate is free to slide upon the upper surface of the base block and a locked position wherein the top plate is locked to the base block.

12. The adjustable die holder of claim 11 wherein n is six and x is eight.

13. The adjustable die holder of claim 11 wherein the second bore is larger than the first bore.

14. The adjustable die holder of claim 11 wherein the second bore is elongated.

15. The adjustable die holder of claim 14 wherein the second bore has an aspect ratio of no more than two.

16. The adjustable die holder of claim 11 wherein the die holding element comprises an upwardly open elongated groove in the top surface of the top plate.

17. The adjustable die holder of claim 16 wherein the die has a rib extending along a bottom surface thereof, the rib being received in the groove in the top plate.

18. The adjustable die holder of claim 16 wherein the second bore is elongated in a direction perpendicular to a major axis of the groove in the top plate.

19. A die and die holder for a press brake, comprising:

a) an adjustable die holding element comprising a pair of laterally opposed ridges defining therebetween an upwardly open elongated groove;

b) an adapter having an upper rib extending along an upper surface thereof and an elongate shank releasably received in the groove in the die holding element; and c) a die having an upper working surface adapted to work in conjunction with a punch to shape sheet material and an elongated channel extending along a bottom surface thereof, the upper rib of the adapter being releasably received in the elongated channel.

20. The die and die holder of claim 19 wherein the shank comprises a lower rib extending downwardly along a lower surface of the adapter.

21. The die and die holder of claim 20 wherein the lower rib is laterally offset from the upper rib.

22. A die and die holder, comprising:

a) a die holding element comprising first and second laterally opposed ridges defining therebetween an upwardly open elongated groove;

b) a first lateral extension releasably carried by the first ridge of the die holding element, the first lateral extension defining an inwardly facing inner surface and defining, with an upper surface of the first ridge, a first die supporting shoulder;

c) a second lateral extension releasably carried by the second ridge of the die holding element, the second lateral extension defining an inwardly facing inner surface and defining, with an upper surface of the second ridge, a second die supporting shoulder; and d) a first die having a shank, the shank being received between the inner surfaces of the first and second lateral extensions and having a lower surface resting on the first and second die supporting shoulders.

23. The die and die holder of claim 22 further comprising a second die exchangeable for the first die, the second die having a shank sized to be received in the upwardly open elongated groove of the die holding element.

24. An adjustable die holder for a press brake comprising:
   a. an elongated base block adapted to be attached to a jaw of a press brake and having a vertical first bore formed therein and a horizontal upper surface;
   b. a top plate slidable on the upper surface of the base block, the top plate bearing a die holding element and having a second bore formed therethrough, the second bore being in substantial alignment with the first bore;
   c. a die carried by the die holding element, the die having a working surface oriented away from the die holding element;
   d. an elongated threaded member extending through the first and second bores, the threaded member having external threads;
   e. an internally threaded element which threadingly mates with the elongated threaded member, and
   f. a handle for rotating the elongated threaded member with respect to the internally threaded element and movable horizontally through an angle between an unlocked position at one side of said angle wherein the top plate is free to slide upon the upper surface of the base block and a locked position at the other side of said angle wherein the top plate is locked to the base block.

25. The adjustable die holder of claim 24 wherein the internally threaded element is positioned beneath the first bore in the base block, the elongate threaded member being attached to the handle for rotation therewith.

26. The adjustable die holder claim 25 wherein the internally threaded element comprises an inner member and a locking ring seated in a recess in the base block having an internal abutting surface; the inner member having internal threads adapted to mate with the external threads of the threaded member and a regular polygonal periphery having n sides; the locking ring having an inner bearing surface defining a regular polygon having an integral multiple of n sides and an outer bearing surface which engages the internal abutting surface of the recess to limit rotation of the locking ring with respect to the base block.

27. The adjustable die holder of claim 24 wherein the internally threaded element comprises an inner member and a locking ring; the inner member having internal threads adapted to mate with the external threads of the threaded member and a regular polygonal periphery having n sides; the locking ring having an inner bearing surface defining a regular polygon having an integral multiple of n sides and an outer bearing surface defining a regular polygon having x sides, wherein x is not an integral multiple of n.

28. The adjustable die holder of claim 27 wherein n is six and x is eight.

29. The adjustable die holder of claim 24 wherein the second bore is larger than the first bore.

30. The adjustable die holder of claim 24 wherein the second bore is elongated.

31. The adjustable die holder of claim 30 wherein the second bore has an aspect ratio of no more than two.

32. An adjustable die holder for a press brake comprising:
   a. an elongated base block adapted to be attached to a jaw of a press brake and having a vertical first bore formed therein, an internally threaded element being positioned adjacent and in alignment with the first bore;
   b. a top plate slidable on an upper surface of the base block, the top plate bearing a die holding element and having a second bore formed therethrough, the second bore being in substantial alignment with the first bore and larger in at least one direction than the first bore;
   c. a die carried by the die holding element, the die having a working surface oriented away from the die holding element;
   d. an elongated threaded member extending downwardly through the first and second bores, the threaded member having external threads mating with internal threads in the internally threaded element; and
   e. a handle attached to the threaded member for rotation therewith and movable horizontally through an angle between an unlocked position at one side of said angle wherein the top plate is free to slide upon the upper surface of the base block and a locked position at the other side of said angle wherein the top plate is locked to the base block, the internally threaded element being positioned beneath the first bore in the base block and rotationally adjustable with respect to the base block to enable adjustment of said angle.

* * * * *